US008243942B2

(12) United States Patent
Grandt

(10) Patent No.: US 8,243,942 B2
(45) Date of Patent: Aug. 14, 2012

(54) HEADPHONES FOR CONNECTION TO AN EXTERNAL ACTIVE NOISE COMPENSATION DEVICE

(75) Inventor: André Grandt, Wedemark (DE)

(73) Assignee: Sennheiser electronic GmbH & Co. KG, Wedemark (DE)

(*) Notice: Subject to any disclaimer, the term of this patent is extended or adjusted under 35 U.S.C. 154(b) by 1005 days.

(21) Appl. No.: 11/918,154

(22) PCT Filed: Apr. 7, 2006

(86) PCT No.: PCT/EP2006/003164

§ 371 (c)(1),
(2), (4) Date: Apr. 4, 2008

(87) PCT Pub. No.: WO2006/105974

PCT Pub. Date: Oct. 12, 2006

(65) Prior Publication Data

US 2009/0041259 A1 Feb. 12, 2009

(30) Foreign Application Priority Data

Apr. 7, 2005 (DE) ........................ 10 2005 016 204

(51) Int. Cl.
*A61F 11/06* (2006.01)
*G10K 11/16* (2006.01)
*H03B 29/00* (2006.01)
*H04R 1/10* (2006.01)

(52) U.S. Cl. .................. 381/71.6; 381/71.1; 381/71.13; 381/72; 381/74

(58) Field of Classification Search ................. 381/71.6, 381/71.13, 72, 71.1, 74
See application file for complete search history.

(56) References Cited

U.S. PATENT DOCUMENTS

| | | | | |
|---|---|---|---|---|
| 4,985,925 | A * | 1/1991 | Langberg et al. | 381/71.6 |
| 5,182,774 | A * | 1/1993 | Bourk | 381/71.6 |
| 5,604,813 | A * | 2/1997 | Evans et al. | 381/71.6 |
| 5,809,156 | A * | 9/1998 | Bartels et al. | 381/370 |
| 6,122,385 | A * | 9/2000 | Konno et al. | 381/96 |
| 6,449,369 | B1 * | 9/2002 | Carme et al. | 381/71.12 |
| 7,065,219 | B1 * | 6/2006 | Abe et al. | 381/74 |
| 7,327,850 | B2 * | 2/2008 | Crump et al. | 381/74 |
| 7,367,422 | B2 * | 5/2008 | Harris et al. | 181/129 |
| 7,489,785 | B2 * | 2/2009 | Donaldson et al. | 381/71.6 |
| 2001/0050993 | A1 * | 12/2001 | Douglas | 381/71.6 |
| 2001/0053228 | A1 * | 12/2001 | Jones | 381/71.6 |
| 2003/0153205 | A1 * | 8/2003 | Corey et al. | 439/106 |
| 2003/0228019 | A1 * | 12/2003 | Eichler et al. | 381/71.8 |
| 2005/0008167 | A1 * | 1/2005 | Gleissner et al. | 381/74 |
| 2008/0013747 | A1 * | 1/2008 | Tran | 381/67 |
| 2009/0310805 | A1 * | 12/2009 | Petroff | 381/318 |

FOREIGN PATENT DOCUMENTS

| | | | |
|---|---|---|---|
| DE | 693 17 827 | | 8/1998 |
| DE | 198 18 925 | | 11/1998 |
| DE | 698 27 245 | | 3/2005 |
| EP | 0658064 | | 6/1995 |
| EP | 658064 | A2 * | 6/1995 |
| WO | 2004/002383 | | 1/2004 |

* cited by examiner

*Primary Examiner* — David Warren
*Assistant Examiner* — Christina Russell
(74) *Attorney, Agent, or Firm* — Frommer Lawrence & Haug LLP

(57) ABSTRACT

There is provided headphones for connection to an external active noise compensation device. The headphones have at least one earphone, a microphone near the ear, and a passive circuitry network for increasing the amplification of the external noise compensation device. In that way noise compensation in respect of the external noise compensation can be increased by increasing the overall amplification by the passive network.

1 Claim, 2 Drawing Sheets

HEADPHONES FOR CONNECTION TO AN EXTERNAL ACTIVE NOISE COMPENSATION DEVICE

CROSS-REFERENCE TO RELATED APPLICATIONS

This application claims priority of International Application No. PCT/EP2006/003164, filed Apr. 7, 2006 and German Application No. 10 2005 016 204.5, filed Apr. 7, 2005, the complete disclosures of which are hereby incorporated by reference.

BACKGROUND OF THE INVENTION a) Field of the Invention

The present invention concerns headphones for connection to an external active noise compensation device and an adaptor unit for connection between an external active noise compensation device and headphones.

b) Description of the Related Art

Headphones with active noise compensation have long been known. In that respect the corresponding electronics for active noise compensation can either be arranged on the headphones or can be in the form of an external unit. External noise compensation units are known for example from aircraft where noise compensation headphones are used in what is referred to as the in-flight entertainment system. Typically, headphones of that kind have a microphone in the region in the proximity of the ear, which serves to detect the interference noise and feed it to the electronics for active noise compensation. Such solutions however frequently only represent proprietary solutions so that the headphones required cannot readily be interchanged with those from another manufacturer.

WO 2004/002383 discloses a noise compensation system and corresponding headphones. The headphones have a microphone for active noise compensation and a filter network which serves to adapt the response characteristic of the microphone to a standardised impedance or response curve.

DE 693 17 827 T2 discloses headphones with an active noise compensation unit and a filter which selectively reduces the level of the high frequency component of the output signal of the microphone in order in that way to reduce the level of the low frequency component of the external noise by the output signal of the electroacoustic transducer.

Attention is further directed to DE 198 18 925 A1, DE 698 27 245 T2, US No 2003/0228019 A1 and U.S. Pat. No. 5,604,813 as general state of the art.

OBJECT AND SUMMARY OF THE INVENTION

The primary object of the present invention is to provide headphones which can be universally employed in relation to active noise compensation.

That object is attained by headphones for connection to an external active noise compensation device comprising at least one earphone, a microphone near the ear, and a passive circuitry network for increasing the amplification of the external noise compensation device. The object is additionally achieved in accordance with the invention by an adaptor unit for connection between an external active noise compensation and headphones comprising a passive circuitry network for increasing the amplification of the external active noise compensation device and for outputting the amplified signal to headphones.

Thus, headphones are provided for connection to an external active noise compensation device. The headphones have at least one earphone, a microphone near the ear and a passive circuitry network for increasing the amplification of the external noise compensation device.

In that way noise compensation in respect of the external noise compensation can be increased by increasing the overall amplification by the passive network.

In accordance with an aspect of the present invention the passive circuitry network is adapted to use the amplification of the external active noise compensation device in such a way that an initiated and/or usable feedback is provided.

The invention further concerns an adaptor unit for connection between an external active noise compensation device and headphones. The adaptor unit has a passive circuitry network for increasing the amplification of the external noise compensation device. The amplified signal is then correspondingly outputted to the headphones.

There is thus provided an adaptor unit which can be connected to noise compensation headphones in order to adapt the headphones to the external active noise compensation device.

Further configurations of the invention are the subject-matter of the appendant claims.

The embodiments by way of example of the invention are described in greater detail hereinafter with reference to the accompanying drawings.

DESCRIPTION OF THE PREFERRED EMBODIMENTS

Figure 1:
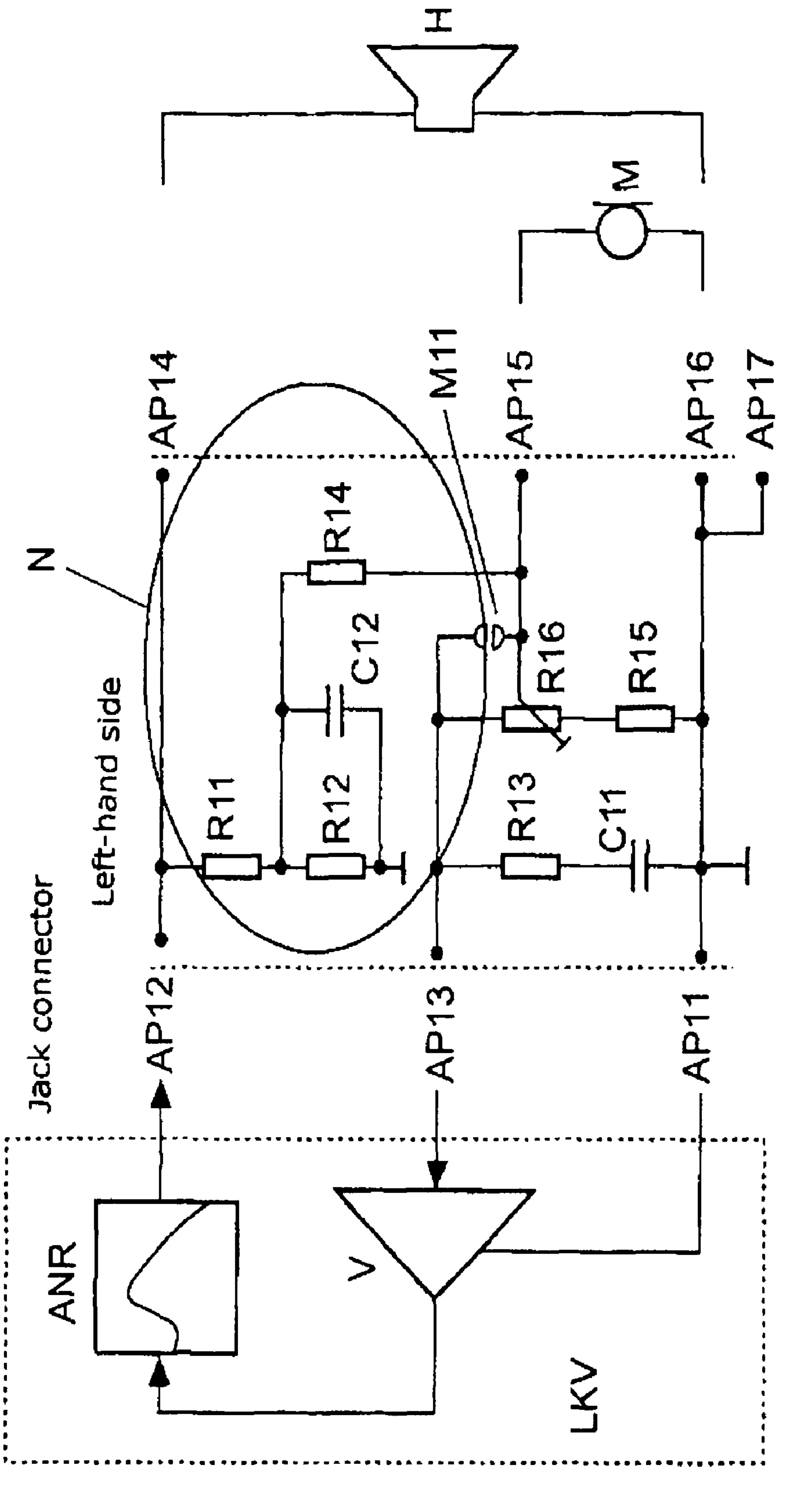
FIG. 1 shows a circuit diagram of noise compensation headphones, an interface between the headphones and an external noise compensation device.

FIG. 1 shows an implementation of a noise compensation headphones. The circuit in FIG. 1 only shows one side of the headphones. The other side of the headphones can be implemented in a similar fashion thereto. An external active noise compensation device LKV comprising an amplifier V and an active noise compensation unit ANR can be connected to a circuitry network having the passive circuitry network N. In addition an earphone H and a microphone M are connected to the network. The passive circuitry network has three resistors R11, R12 and R14 and optionally a capacitor C 12. The earphone H of the headphones is connected to the terminals AP14 and AP16 of the network. The microphone is connected to the terminals AP15 and AP16. The output AP11 controls the amplification of the amplifier V in the external active noise compensation device LKV and the output AP13 represents the signal to be amplified by the external noise compensation device. The amplified signal is passed to the active noise compensation unit ANR where corresponding noise compensation is carried out. The output of the noise compensation unit ANR is passed to the terminal AP12, such as for example to an in-flight stereo jack, of the network. The resistors R11 and R12 are connected in series between the terminal AP12 and ground. The resistor R14 is connected between the terminal AP15 and the connection between the resistors R11 and R12. The capacitor C12 is connected in parallel to the resistor R12.

The configuration of the circuitry network N with the three resistors and optionally the capacitor C12 increases the loop gain. In other words, the network N uses the gain of the external active noise compensation device in order to achieve an initiated usable feedback.

The above-described network can be implemented in the headphones or in a housing on the cable of the headphones or however in an adaptor unit which can be connected to the headphones. The adaptor unit can also be provided between the external active noise compensation device and the headphones.

Alternatively or additionally thereto, a network as described above can be implemented in the external active noise compensation device.

The gain achieved thereby in terms of the efficiency of active noise compensation is dependent on the acoustics, the position of the resistor R16 and the further resistors. In a frequency range of between 200 Hz and 500 Hz an increase in compensation by >5 dB is achieved without reducing the stability of the system.

Figure 2:
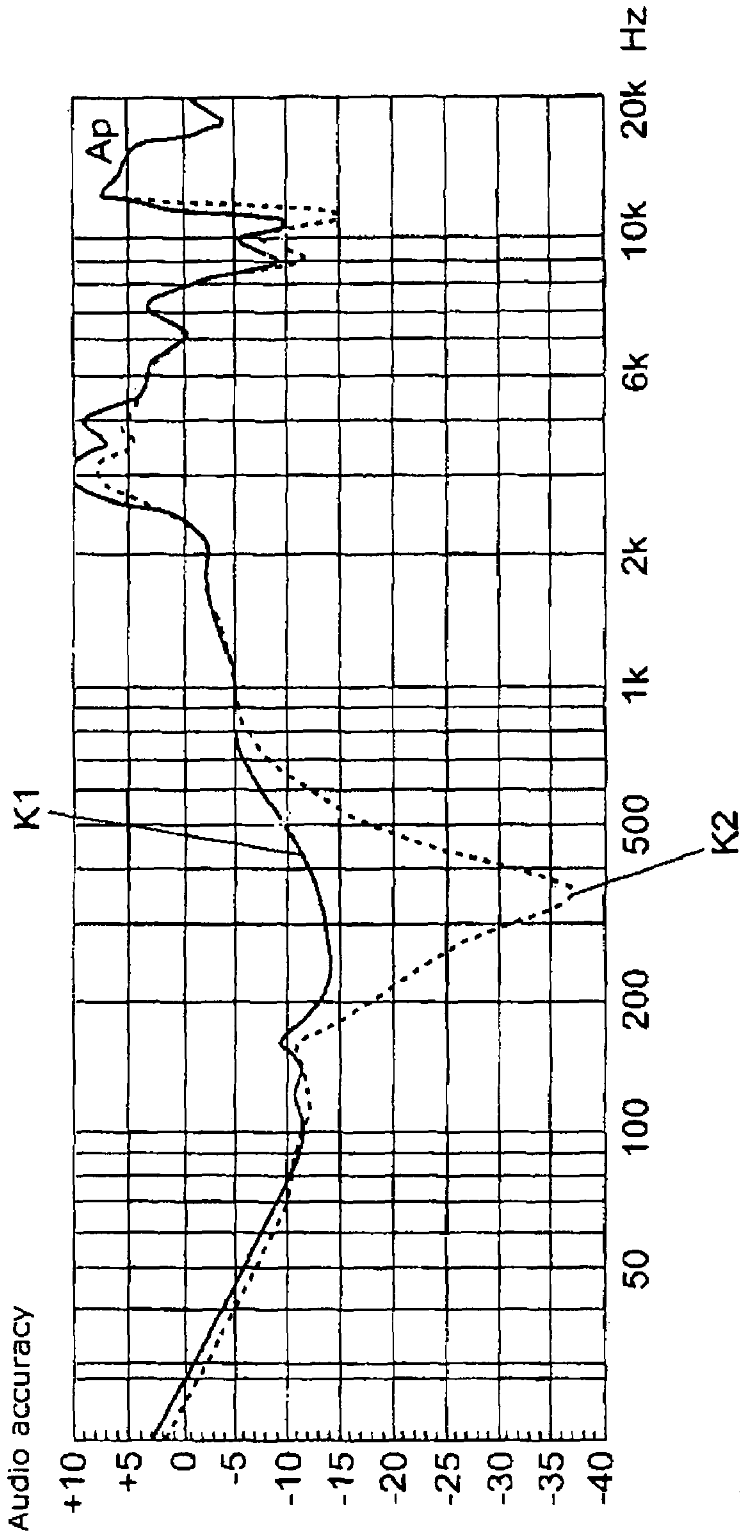
FIG. 2 shows a graph in respect of measurements of the compensation effect.

FIG. 2 shows a graph in respect of the compensation achieved. The upper graph K1 represents in that respect the compensation achieved without the circuitry network N while the lower curve K2 shows the compensation with the corresponding circuitry network. In particular the measurements in FIG. 2 show the influence of the network for a very high positive feedback component, that is to say the resistor R14 is small and the resistor R16 is large. The deviations in value between the two measured curves occur between 200 and 700 Hertz.

The advantages of the above-described arrangement represent increased compensation in respect of active noise compensation. Furthermore different headphones can be combined with already existing active noise compensation units without adaptation of the acoustics having to be effected. The basic idea of the invention can be implemented for example in aviation (for example in an aircraft seat), in the consumer field (for example in a motor vehicle seat or in a seat in a streetcar or tram, a train or in a subway) and in the military sector. That is preferably effected when noise compensation headphones are to be connected to an external electronic system of active noise compensation. In that way it is possible to avoid adaptation of the acoustics of the headphones to the corresponding external noise compensation units.

While the foregoing description and drawings represent the present invention, it will be invention, it will be obvious to those skilled in the art that various changes may be made therein without departing from the true spirit and scope of the present invention.

Reference Numerals:

AP11 output
AP12 terminal
AP13 output
AP14 terminal
AP15 terminal
AP16 terminal
AP17 terminal
C11 capacitor
C12 capacitor
R11 resistor
R12 resistor
R13 resistor
R14 resistor
R15 resistor
R16 resistor

The invention claimed is:

1. Headphones for connection to an external active noise compensation device comprising:

at least a first terminal and a second terminal, to which the external active noise compensation device can be coupled;

at least one earphone for receiving electrical signals from the external active noise compensation device via the first terminal;

a microphone near an ear for picking up sound near the ear and being eclectically coupled to the second terminal to forward a signal to be amplified by the external noise compensation device; and a passive circuitry network having at least one resistor and being configured so that an output of the passive circuitry network is joined with the signal from the microphone to create an output signal to be amplified by the external noise compensation device;

wherein the passive circuitry network is configured to provide an initiated feedback for the external noise compensation device;

wherein the passive circuitry network is coupled between the first and second terminals.

* * * * *